United States Patent
Park et al.

(10) Patent No.: US 8,859,567 B2
(45) Date of Patent: Oct. 14, 2014

(54) HYDRATE OF 1-{(2S)-2-AMINO-4-[2,4-BIS(TRIFLUOROMETHYL)-5,8-DI-HYDRO-PYRIDO[3,4-D]PYRIMIDIN-7(6H)-YL]-4-OXOBUTYL}-5,5-DIFLUORO-PIPERIDIN-2-ONE TARTRATE

(75) Inventors: Ki Sook Park, Daejeon (KR); Jung Min Yun, Daejeon (KR); Bong Chan Kim, Daejeon (KR); Kyu Young Kim, Daejeon (KR); Ji Hye Lee, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 13/879,571

(22) PCT Filed: Oct. 31, 2011

(86) PCT No.: PCT/KR2011/008186
§ 371 (c)(1),
(2), (4) Date: Apr. 15, 2013

(87) PCT Pub. No.: WO2012/060590
PCT Pub. Date: May 10, 2012

(65) Prior Publication Data
US 2013/0203787 A1  Aug. 8, 2013

(30) Foreign Application Priority Data
Nov. 1, 2010 (KR) ........................ 10-2010-0107868

(51) Int. Cl.
*C07D 471/04* (2006.01)
*A61K 31/519* (2006.01)

(52) U.S. Cl.
CPC ................................... *C07D 471/04* (2013.01)
USPC .................. 514/264.1; 514/258.1; 544/279; 546/118

(58) Field of Classification Search
CPC ............................. C07D 471/04; A61K 31/519
USPC .............. 514/264.1, 258.1; 544/279; 546/118
See application file for complete search history.

(56) References Cited

U.S. PATENT DOCUMENTS

| 2006/0040963 | A1 | 2/2006 | Mathvink et al. |
| 2006/0074087 | A1 | 4/2006 | Ashton et al. |
| 2008/0188471 | A1 | 8/2008 | Lee et al. |

FOREIGN PATENT DOCUMENTS

| KR | 10-2006-0105609 A | 10/2006 |
| KR | 10-0776623 B1 | 11/2007 |
| WO | WO 2006/104356 A1 | 10/2006 |

OTHER PUBLICATIONS

Morris, K.R. et al, "Characterization of humidity-dependent changes in crystal properties of a new HMG-CoA reductase inhibitor in support of its dosage form development," International Journal of Pharmaceutics, 1994, vol. 108, pp. 195-206.
International Search Report issued in PCT/KR2011/008186, mailed on May 1, 2012.

*Primary Examiner* — Sreeni Padmanabhan
*Assistant Examiner* — Irina Neagu
(74) *Attorney, Agent, or Firm* — Birch, Stewart, Kolasch & Birch, LLP

(57) ABSTRACT

The present invention relates to 1.5 hydrate of of 1-{(2S)-2-amino-4-[2,4-bis(trifluoromethyl)-5,8-dihydropyrido[3,4-d]pyrimidin-7(6H)-yl]-4-oxobutyl}-5,5-difluoropiperidin-2-one tartrate, a process for preparing the same, and a pharmaceutical composition for inhibiting DPP-IV, which comprises said compound as the active component.

6 Claims, 16 Drawing Sheets
(13 of 16 Drawing Sheet(s) Filed in Color)

HYDRATE OF 1-{(2S)-2-AMINO-4-[2,4-BIS(TRIFLUOROMETHYL)-5,8-DI-HYDRO-PYRIDO[3,4-D]PYRIMIDIN-7(6H)-YL]-4-OXOBUTYL}-5,5-DIFLUORO-PIPERIDIN-2-ONE TARTRATE

This application is a National Stage of International Application No. PCT/KR11/08186, filed on 31 Oct. 2011, which claims the benefit of Korean Patent Application No. 10-2010-0107868, filed on 1 Nov. 2010.

TECHNICAL FIELD

The present invention relates to 1.5 hydrate of 1-{(2S)-2-amino-4-[2,4-bis(trifluoromethyl)-5,8-dihydropyrido[3,4-d]pyrimidin-7(6H)-yl]-4-oxo-butyl}-5,5-difluoropiperidin-2-one tartrate represented by the following formula 1 (hereinafter, referred to as "Compound 1"), and a process for preparing the same.

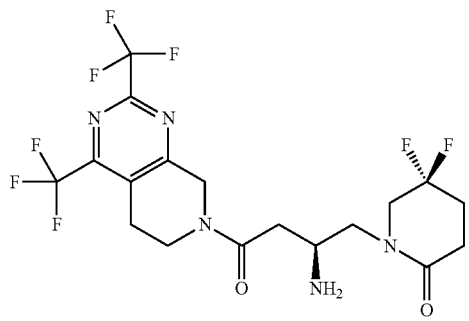

(1)

BACKGROUND ART

Compound 1 is disclosed in Korean Patent Application No. 10-2006-0029138, which is incorporated herein by reference in its entirety, and exhibits superior inhibitory activity against dipeptidyl peptidase-IV (DPP IV) and thus is useful as an agent for treating diabetes. Typical examples of diseases caused by DPP IV can include, but are not limited to, diabetes, obesity, etc. Among diabetes, it is particularly useful for the treatment and prevention of type II diabetes. The term "treatment" as used above means that when the compound is used for individuals manifesting symptoms of a disease, it can interrupt or delay the progress of disease; and the term "prevention" as used above means that when the compound is used for individuals who do not manifest symptoms of a disease but have the risk of onset of disease, it can interrupt or delay the sign of disease.

The investigation of physical and chemical properties of a new drug is necessary for efficient and successful development of the new medicine. Particularly, by studying the presence of polymorphs and pseudopolymorphs of the drug and differences in physical and chemical properties between respective polymorphs the preferable crystal form of the drug can be selected in view of the pharmaceutical aspect (Remington's Pharmaceutics, Chapter 75 Preformulation); (Byrn, S. R., Solid State Chemistry of Drugs, Academic Press, New York, 1982). When the polymorphs are present in the solution, they are chemically identical, but in the solid state they respectively have definitely different X-ray diffraction patterns and exhibit differences in various physical and chemical properties. Particularly, respective polymorphs can have differences in bioavailability due to the differences in dissolution rates, and exhibit unexpected properties in the aspect of thermodynamic stability.

When a certain drug is present in the form of polymorphs, the crystal forms having different structures can be obtained depending on the conditions of recrystallization such as recrystallizing solvent, drug concentration, heating and cooling rates, temperature, stirring rate, and the like, during the procedures for preparing the drug. Therefore, in order to obtain the same crystal form a special attention is required for the management of manufacturing procedures.

Hydrates as one of pseudopolymorphs comprise a water molecule within the crystal of drug, and have a crystal form different from anhydrate. Difference in the crystal structure can be distinguished by X-ray diffraction pattern. Since in hydrates only physical properties such as crystallinity, hygroscopic property, melting point, solubility, dissolution rate, etc. are changed without any change of chemical properties providing pharmacological effects, they have a very important significance in the pharmaceutical aspect, like polymorphs (Morris, K. R. et al., Int. J. Pharm., 108, 1994, 195-206).

The knowledge which is understood up to date from various references relating to the technical field to which the present invention belongs is that there is no general tendency, for example, to prefer the hydrate to the anhydrate or vice versa, for the improvement of pharmaceutical properties including drug stability, hygroscopic property, etc. Ultimately, determination of the forms having the optimal pharmaceutical properties for respective compounds must be made by a person skilled in the relevant technical field through continuous study case by case.

Particularly, it can never be anticipated among any contemplable forms of a certain drug, i.e. free compound, salt, anhydrate and hydrate, which one can exhibit a stability with the hygroscopic property that is not changed depending on the surrounding humidity. Furthermore, among the hydrates the most stable hydration number cannot be predicted. And, even though the hydration number is the same, it is also unpredictable which crystal form would be the most stable. This is a phenomenon that is inconsistently revealed since it cannot be anticipated and belongs to the experimental area which can be confirmed only through repeated experiments.

DISCLOSURE OF INVENTION

Technical Problem

Thus, the present inventors conducted intensive study to provide a stable polymorph or pseudopolymorph of Compound 1. As a result, we have surprisingly found that 1.5 hydrate of tartrate salt of Compound 1 exhibits a superior stability against the change of relative humidity as compared to the anhydrate or other hydrates having a similar hydration number, and thus, completed the present invention. Up to date, the crystal form of Compound 1 has never been publicly disclosed.

Solution to Problem

Therefore, the present invention provides 1.5 hydrate of tartrate salt of Compound 1.

In addition, the present invention provides a process for preparing 1.5 hydrate of tartrate salt of Compound 1.

Advantageous Effects of Invention

Since 1.5 hydrate of tartrate salt of Compound 1 obtained as a crystal form that can be developed according to the present invention, is superior to the similar crystal forms in terms of a stability, particularly, a storage stability, it can be very advantageously used in preparing the pharmaceutical composition containing Compound 1 as an active component. That is, 1.5 hydrate according to the present invention neither loses any water molecule in the crystal nor accepts water molecules any more in the broad range of relative humidity to maintain the water content thereof, and therefore, shows substantially no change of weight depending on the change of humidity. In case of unstable crystal forms, the water content thereof can vary with environments or additives during the storage and formulation process. For instance, in quantifying the standard material and the sample for the purpose of quantification, if the experiment is not conducted in a drying room, some experimental error may be caused to incur the problems of quality control. However, since in the 1.5 hydrate according to the present invention the water content does not sensitively vary with environments in the broad range of relative humidity, the product with a uniform standard can always be obtained during the storage and formulation process, and further, an error in the quality control is very small. As above, the 1.5 hydrate according to the present invention shows a great advantage in terms of handling and quality control.

Further, 1.5 hydrate of tartrate salt of Compound 1 according to the present invention does not show any change in the crystal form depending on the change of humidity. On the contrary, the present inventors have identified that 0.5 hydrate and anhydrate of tartrate salt of Compound 1 absorb much water as the relative humidity is raised, to be converted into a more stable 1.5 hydrate according to the present invention. It was also identified that even in the experiment for an accelerating stability (40° C./75% RH) the 0.5 hydrate is converted into the 1.5 hydrate after a lapse of some hours.

In addition, it is possible to control the preparation of 1.5 hydrate of tartrate salt of Compound 1 according to various methods as provided in the present invention.

BRIEF DESCRIPTION OF DRAWINGS

The patent or application file contains at least one color drawing. Copies of this patent or patent application publication with color drawing will be provided by the USPTO upon request and payment of the necessary fee.

MODE FOR THE INVENTION

As identified to respectively have the characteristic crystal forms according to the present invention, in the present specification the 1.5 hydrate of tartrate salt of Compound 1 is designated as "the crystal form I"; the 0.5 hydrate is designated as "the crystal form II"; and the anhydrate is designated as "the crystal form III". Herein, the water content of 1.5 hydrate is 3.0~5.5%, that of 0.5 hydrate is 1.0~2.5%, and that of anhydrate is 0~1.0%.

Figure 1:
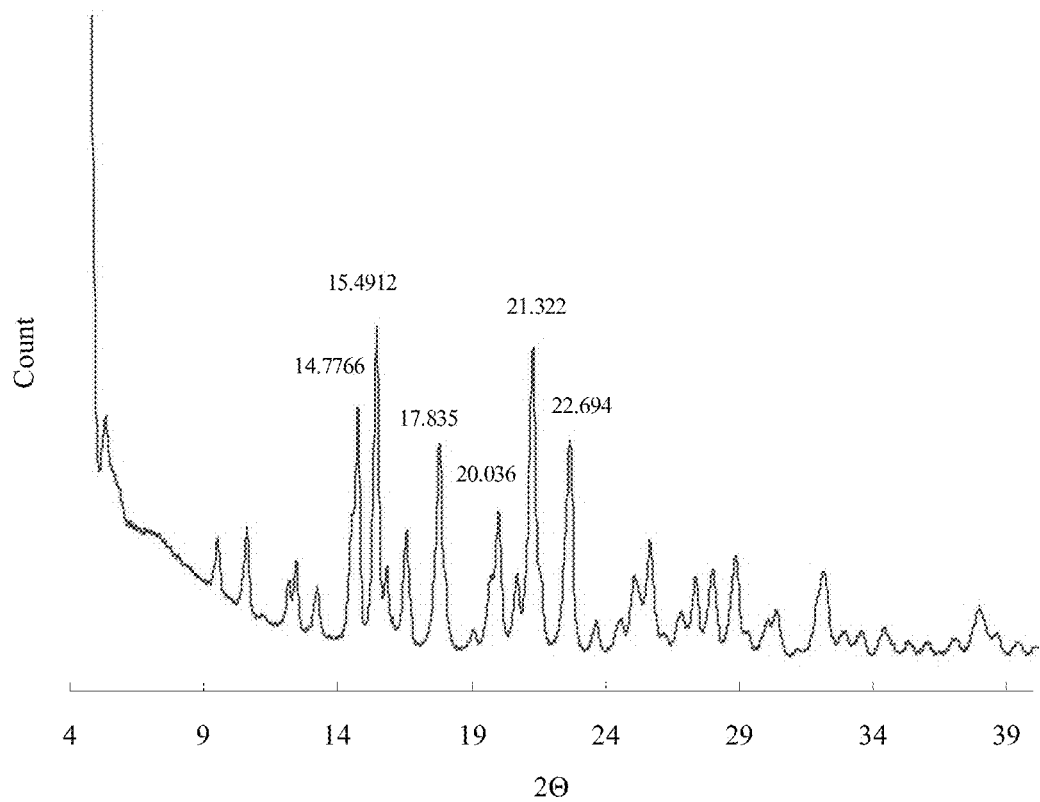
FIG. 1 represents the X-ray powder diffraction (XRD) spectrum of the crystal form I as the 1.5 hydrate of tartrate salt of Compound 1.
Figure 5:
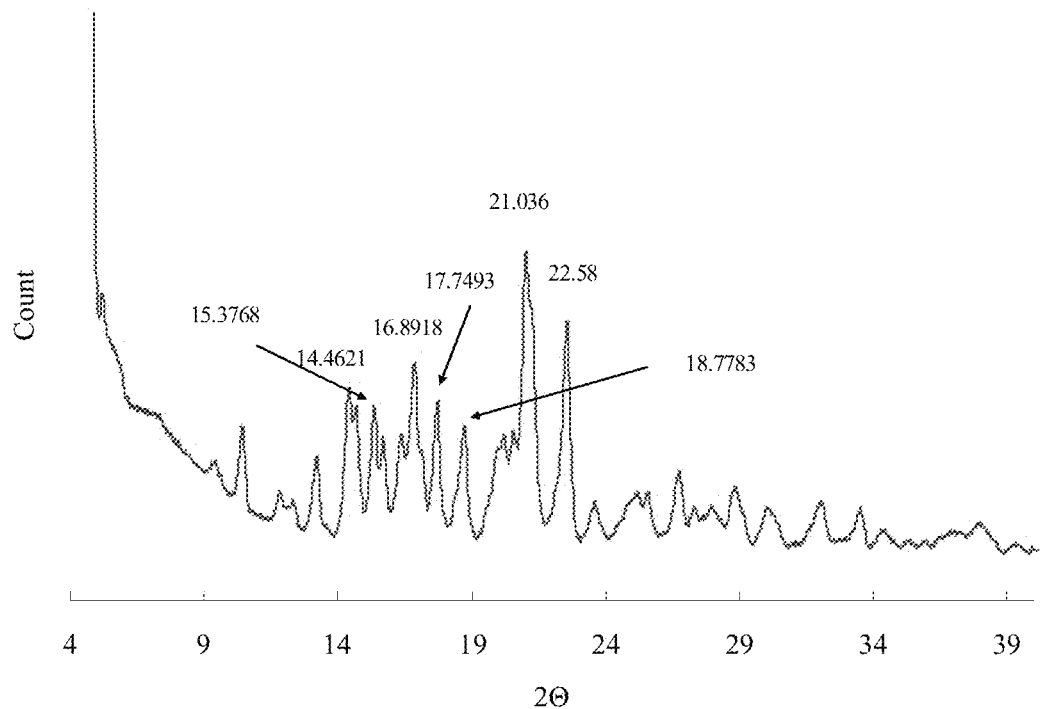
FIG. 5 represents the X-ray powder diffraction (XRD) spectrum of the crystal form II as the 0.5 hydrate of tartrate salt of Compound 1.
Figure 10:
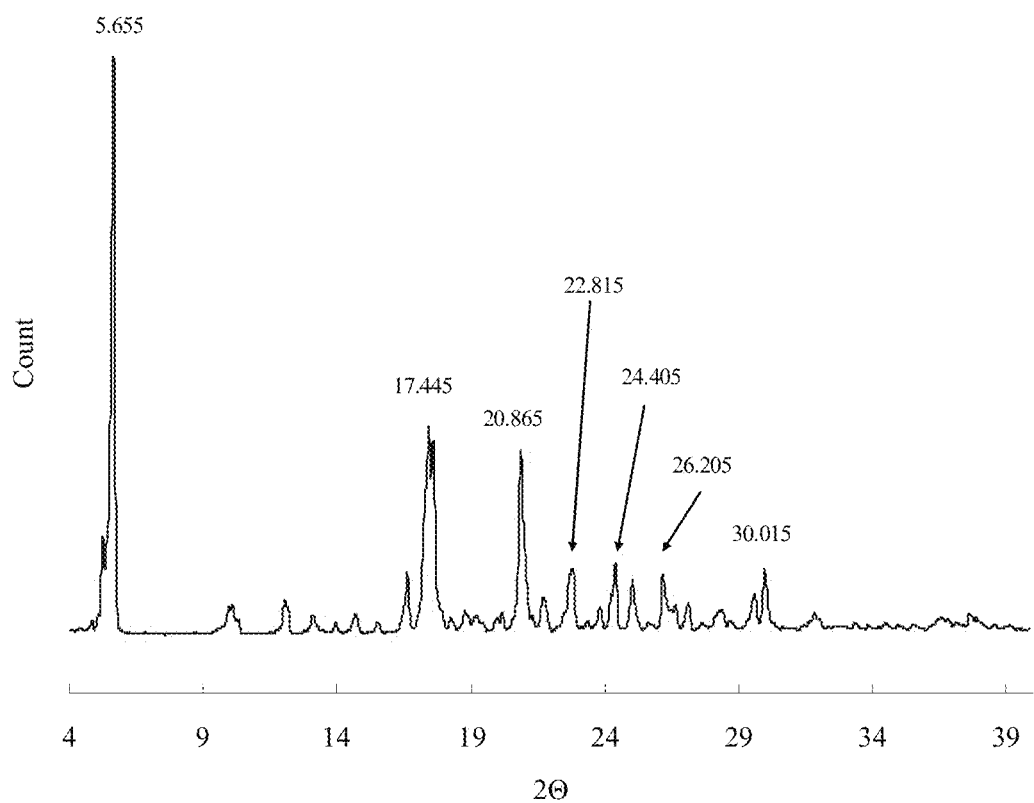
FIG. 10 represents the X-ray powder diffraction (XRD) spectrum of the crystal form III as the anhydrate of tartrate salt of Compound 1.

The crystallinities of the crystal forms I, II and III are different from each other as can be identified from X-ray diffraction diagrams shown in FIGS. 1, 5 and 10.

Figure 3:
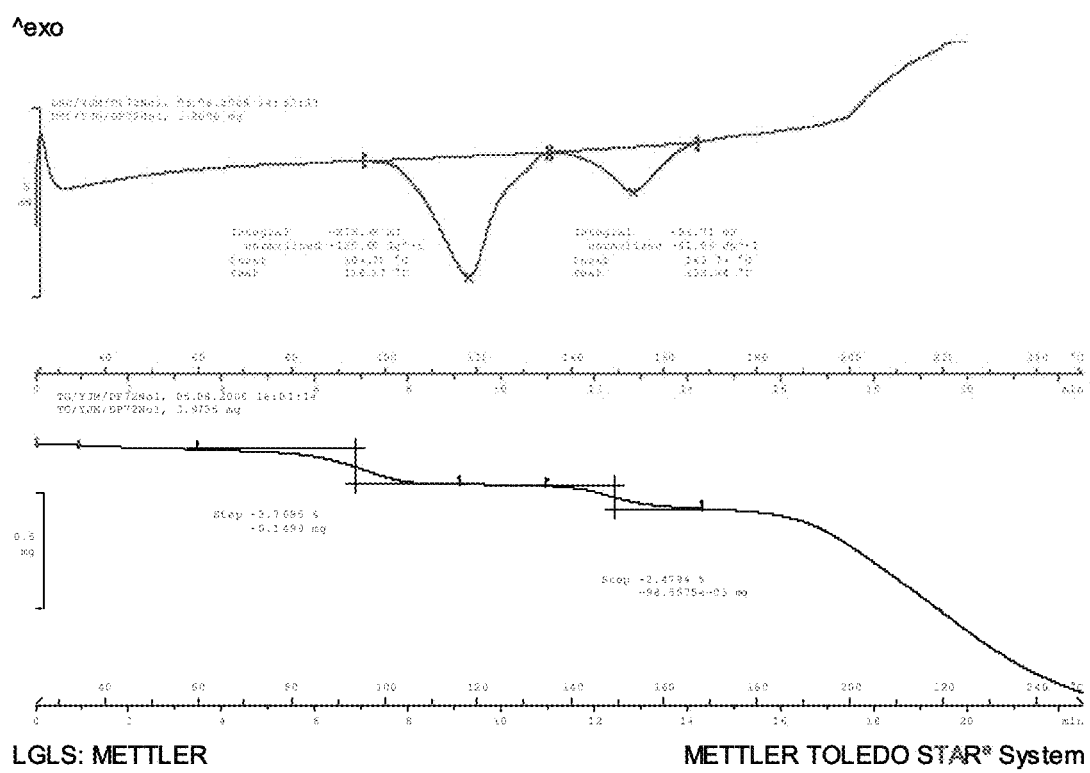
FIG. 3 represents the result of Differential scanning calorimetric (DSC) or Thermogravimetric (TG) analysis of the crystal form I as the 1.5 hydrate of tartrate salt of Compound 1.
Figure 7:
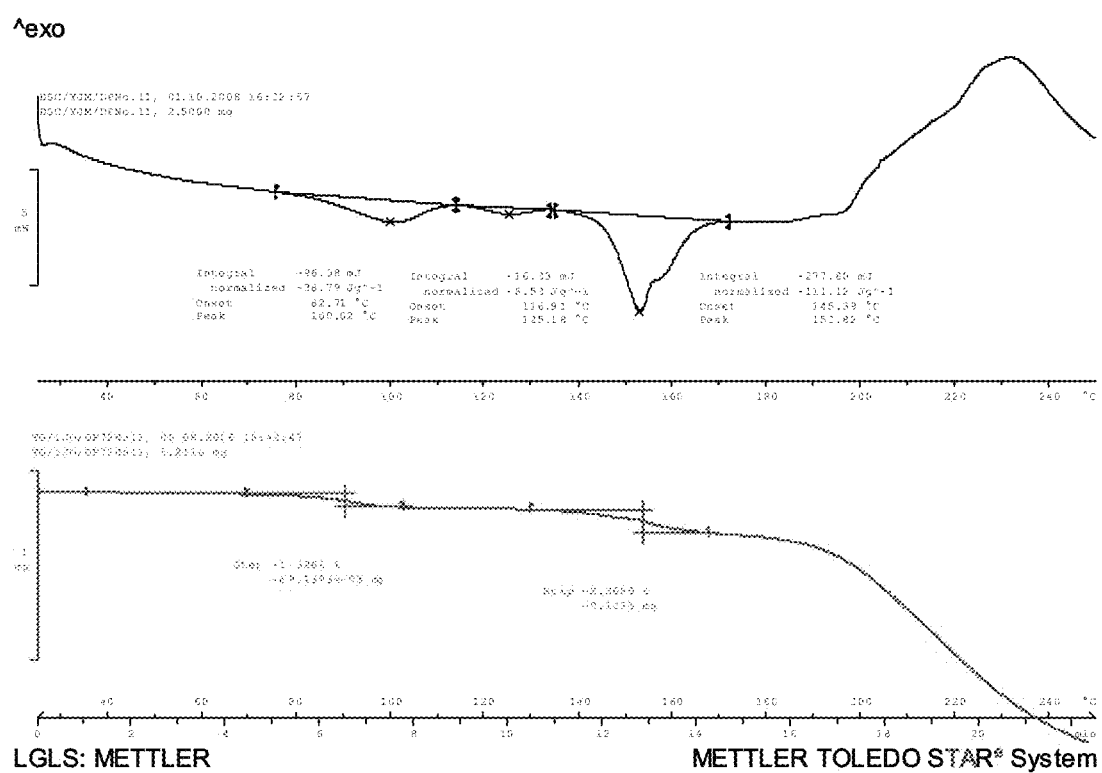
FIG. 7 represents the result of Differential scanning calorimetric (DSC) or Thermogravimetric (TG) analysis of the crystal form II as the 0.5 hydrate of tartrate salt of Compound 1.
Figure 12:
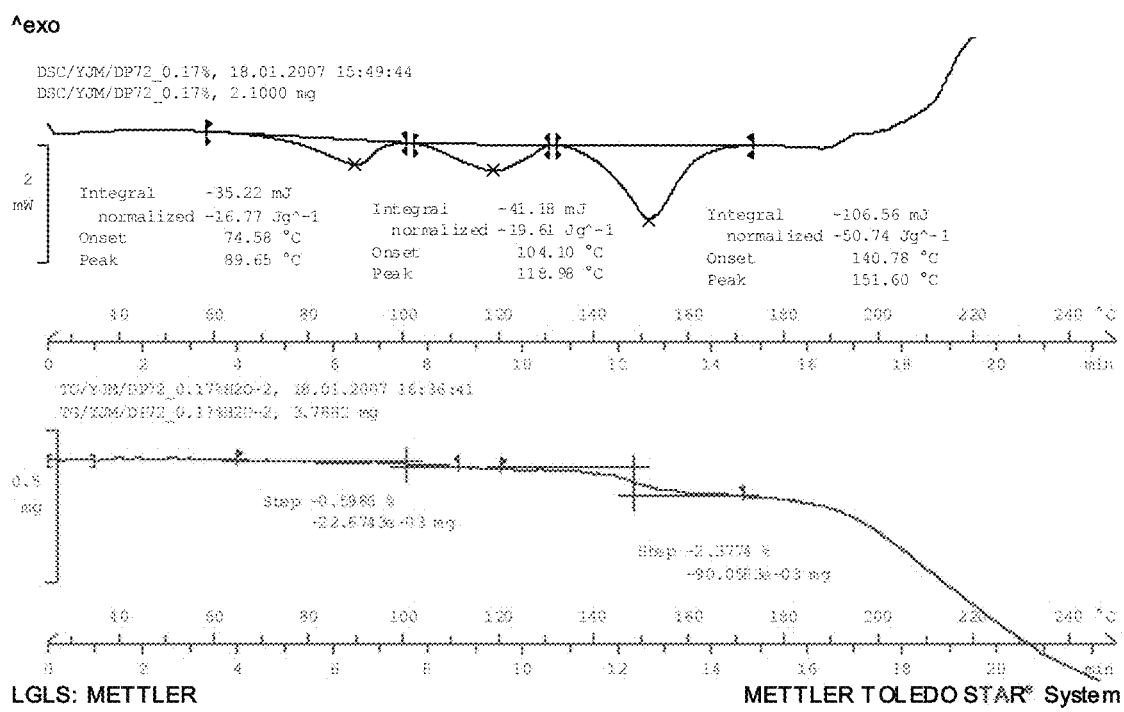
FIG. 12 represents the result of Differential scanning calorimetric (DSC) or Thermogravimetric (TG) analysis of the crystal form III as the anhydrate of tartrate salt of Compound 1.

As a result from the analysis by Differential Scanning calorimetry for the crystal form I, the endothermic peak occurring with releasing water contained in the crystal lattice at 90~130° C. has a broad section in which the melting point is included, and the endothermic peak occurs one more time in the section of 130~160° C. with undergoing the chemical dehydration of tartrate salt of Compound 1. In addition, the thermogravimetric analysis shows the weight loss of about 4.0% that is equivalent to the water contained in the lattice in the first endothermic section of differential scanning calorimetry and the weight loss of about 2.5% that is equivalent to the water removed by dehydration from the structure of tartrate salt of Compound 1 in the second endothermic section (FIG. 3). The analysis for the crystal forms II and III by Differential Scanning calorimetry shows three endothermic points. Specifically, the first endothermic point occurs with releasing water contained in the lattice, the second endothermic point occurs with the melting point, and the third endothermic point occurs via chemical dehydration reaction. Further, according to the thermogravimetric analysis the first endothermic section shows the weight loss that is equivalent to the water contained in the lattice (about 1.3% in the crystal form II, and about 0.6% in the crystal form III), and the third endothermic section shows the weight loss of about 2.4% that is equivalent to the water removed by dehydration (FIGS. 7 and 12). Since the water content in the lattice of tartrate salt of Compound 1 as above was consistent with the water content quantified by Karl-Fischer method (Mettler Toledo DL37 KF Coulometer), it was proved that the endothermic peaks were caused by evaporation of water molecules.

Hereinafter, we intend to explain that the crystal form I according to the present invention has unexpected superior characteristics from any aspect in comparison with other crystal form II or III by more specifically comparing the characteristics of respective crystal forms.

Crystal Form I

The present invention relates to the crystal form of 1.5 hydrate of tartrate salt of Compound 1. As a result of the analysis of the properties thereof the crystal form I exhibits the following characteristics:

(a) The water content of the crystal form I is in the range of 3.0~5.5%.

(b) The characteristic peak values (2θ) of XRD spectrum measured at CuKα, 40 kV, 30 mA are 15, 18, 20, 21 and 23°.

(c) Infrared (IR) spectrum shows a characteristic absorbance at about 3591, 3401, 3128, 1712, 1655, 1636, 1229, 1205, 1129 and 1058 $cm^{-1}$.

(d) Differential scanning calorimetry spectrum shows the endo-thermal peaks in two broad temperature ranges of about 90~130° C. and 130~160° C.

(e) The water content measured by Karl-Fisher method is about 4.0%.

(f) When the temperature is raised from 25° C. to 250° C., the weight loss of about 4.0% and about 2.5% occur in the range of 70~110° C. and 140~170° C., respectively (This is the result obtained from TG of FIG. 3. Since energy change occurs slightly later than the weight change, there is generally a difference between the results of DSC and TG.).

(g) Tartrate salt of Compound 1 can be crystallized from water, acetonitrile/water, ethanol/water, ethanol/hexane or ethyl acetate/hexane solvent, and preferably crystallized from water.

(h) Crystal form I can be prepared by subjecting the crystal form II or III to moisture absorption.

(i) The weight change is absent or, if any, 0.8% or less depending on the change of external humidity in the range of 5~95% RH, and the crystal form is not changed with the change of humidity.

Crystal Form II

In order to find out other crystal forms than the crystal form I the present inventors prepared 0.5 hydrate of tartrate salt of Compound 1 (crystal form II). Although the 0.5 hydrate is the same tartrate salt of the same compound and has a similar hydration number, it shows unstable storage stability as follows, in comparison with the 1.5 hydrate (crystal form I).

(a) The water content of the crystal form II is in the range of 1.0~2.5%.

(b) The characteristic peak values (2θ) of XRD spectrum measured at CuKα, 40 kV, 30 mA are 14, 15, 17, 18, 19, 21 and 23°.

(c) Infrared (IR) spectrum shows a characteristic absorbance at about 3455, 2891, 1721, 1655, 1571, 1228, 1209, 1131, 1086 and 1059 $cm^{-1}$.

(d) Differential scanning calorimetry spectrum shows the endo-thermal peaks in three broad temperature ranges of about 80~115° C., 115~135° C. and 135~173° C., and the melting point at about 117° C.

(e) The water content measured by Karl-Fisher method is about 2.0%.

(f) When the temperature is raised from 25° C. to 250° C., the weight loss of about 1.3% and about 2.4% occur in the range of 70~104° C. and 137-168° C., respectively.

(g) The weight change of 4.0% or more occurs over the change of external humidity in the range of 5~95% RH and moisture is rapidly absorbed from 45% RH, giving a weight increase of 3.7% at 75% RH. If a total of 4.0% or more moisture is contained, the crystal form II is converted into the crystal form I. It has been shown that the crystal form II is converted into the crystal form I from about 60% RH (see FIGS. 8 and 9). That is, the crystal form varies with the change of humidity to reach the more stable crystal form I. In addition, it is converted into the crystal form I within 8 weeks in the accelerating (40° C./75% RH) stability test.

Crystal Form III

In order to find out other crystal forms than the crystal form I the present inventors prepared anhydrate of tartrate salt of Compound 1 (crystal form III). The anhydrate shows unstable storage stability as follows, in comparison with the 1.5 hydrate (crystal form I).

(a) The water content of the crystal form III is in the range of 0~1.0%.

(b) The characteristic peak values (2θ) of XRD spectrum measured at CuKα, 40 kV, 30 mA are 6, 17, 21, 23, 24, 26 and 30°.

(c) Infrared (IR) spectrum shows a characteristic absorbance at about 3470, 3187, 2940, 1640, 1570, 1229, 1206, 1130 and 1056 $cm^{-1}$.

(d) Differential scanning calorimetry spectrum shows the endo-thermal peaks in three broad temperature ranges of about 65~100° C., 100~130° C. and 132~170° C., and the melting point at about 104° C.

(e) The water content measured by Karl-Fisher method is about 0.1%.

(f) When the temperature is raised from 25° C. to 250° C., the weight loss of about 0.6% and about 2.4% occur in the range of 62~110° C. and 120~173° C., respectively.

Figure 13:
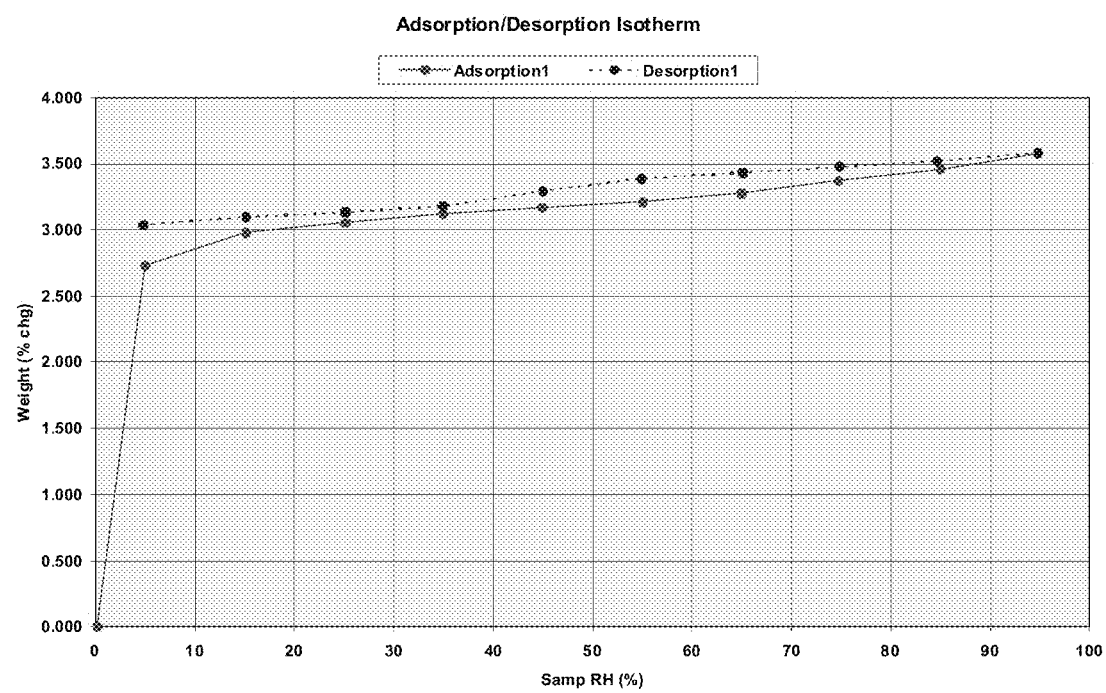
FIG. 13 represents the dynamic vapor adsorption/desorption isotherm of the crystal form III as the anhydrate of tartrate salt of Compound 1.
Figure 14:
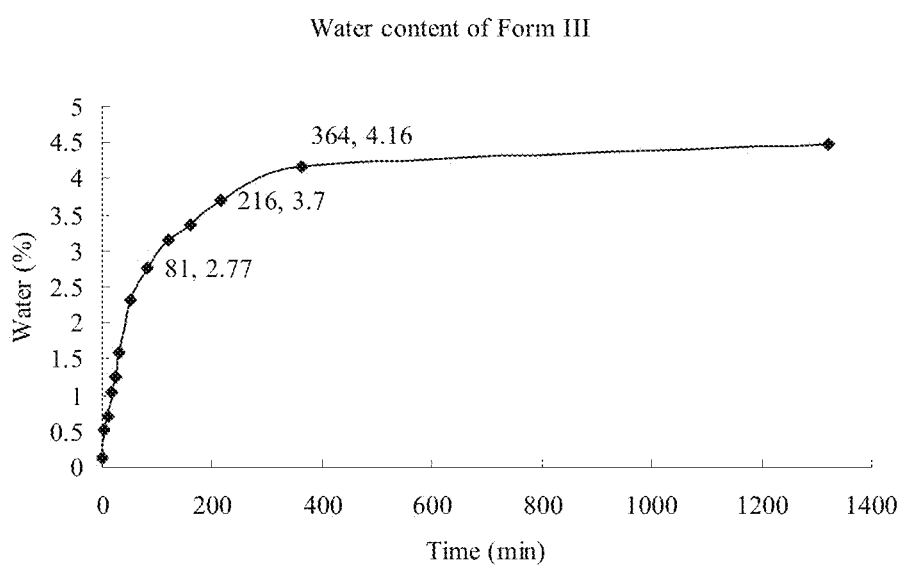
FIG. 14 represents the moisture adsorption curve of the crystal form III as the anhydrate of tartrate salt of Compound 1, with time lapse at normal temperature and normal humidity.
Figure 15:
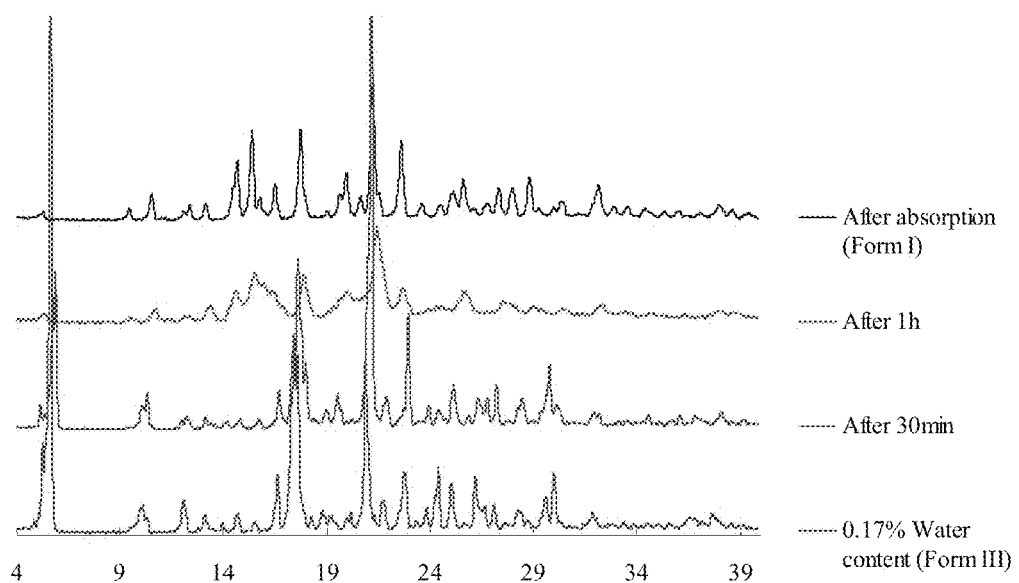
FIG. 15 represents the X-ray powder diffraction (XRD) spectrum of the crystal form III as the anhydrate of tartrate salt of Compound 1, during the moisture adsorption study.

(g) The weight change of 3.5% or more occurs over the change of external humidity in the range of 5~95% RH and moisture is rapidly absorbed from 5% RH, so that the crystal form III is converted into the crystal form I from about 15% RH (see FIGS. 13, 14 and 15). That is, the crystal form varies with the change of humidity to arrive at the more stable crystal form I.

The above results suggest that in the range of relative humidity under which the formulation is conventionally practiced the crystal forms II and III are unstable and thus automatically converted into the crystal form I. Such tendency is shown more remarkably in case of the crystal form III.

1.5 Hydrate of tartrate salt of Compound 1 according to the present invention exhibits a strong DPP-IV inhibitory activity in the same way as the corresponding free base disclosed in Korean Patent Application No. 10-2006-0029138. In addition, the 1.5 hydrate of the present invention shows improved physical and chemical properties as compared to the crystal forms having other hydration state. Therefore, the 1.5 hydrate according to the present invention is considerably easy to handle, quality control and formulate as compared to the crystal forms having other hydration state.

The 1.5 hydrate according to the present invention has the DPP-IV inhibitory activity as mentioned above, and therefore, can be formulated for convenient administration in the pharmaceutical and veterinary field. Formulation can be conducted according to the techniques and methods known in the art in relation to other formulations having DPP-IV inhibitory activity, particularly with reference to the disclosure of Korean Patent Application No. 10-2006-0029138 which is incorporated herein by reference in its entirety.

Therefore, a pharmaceutical composition for inhibiting DPP-IV, comprising the 1.5 hydrate according to the present invention as the active component together with a pharmaceutically acceptable carrier, is covered by the scope of the present invention. The composition according to the present invention is characterized in that it is used particularly for the treatment and prevention of diabetes or obesity.

The present invention is illustrated more in detail by means of the following Examples and Test Examples. However, the following Examples and Test Examples are provided only to assist the understanding of the present invention but it is not intended that the scope of the present invention is limited in any manner by these Examples and Test Examples.

Example 1

Preparation of 1.5 Hydrate of Tartrate Salt of Compound 1 (Crystal Form I)

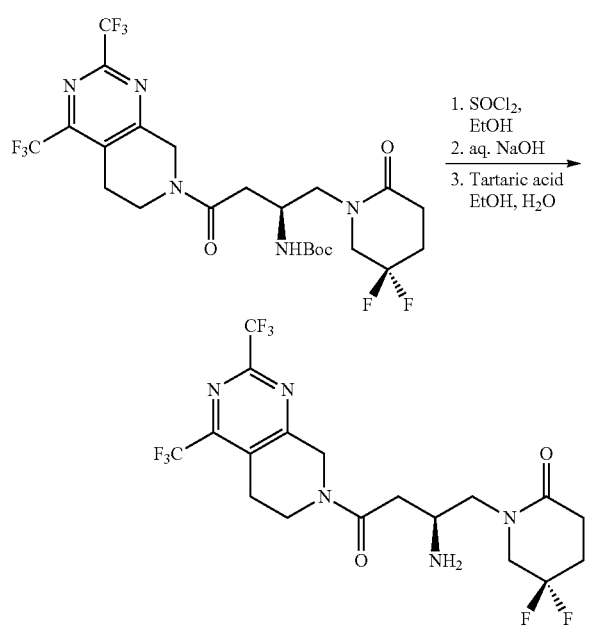

1.87 kg of the compound 2 was dissolved in about 9 L of ethanol. 0.94 kg of SOCl$_2$ was added at 0~10° C. and then stirred while maintaining low temperature. After concentrating under reduced pressure, the concentrate was dissolved in 11.2 L of MTBE (methyl t-butyl ether), and the resulting mixture was adjusted with 10 N NaOH solution to pH 7~8. After separating the layers, the aqueous layer was extracted with about 3.7 L of MTBE and twice with 3.7 L of MTBE, and then concentrated under reduced pressure. The resulting brown turbid solution was dissolved in 12 L of ethanol, 0.47 kg of L-tartaric acid dissolved in about 1.5 L of water was added thereto, and then stirred for 1 hour. The resulting crystalline slurry was filtered, washed with water and ethanol (1:8), and then dried to obtain 1.13 kg (yield 97.5%) of the title compound.

$^1$H NMR (500 MHz, CD$_3$OD) δ2.38 (m, 2H), 2.59 (m, 2H), 2.82-2.99 (m, 2H), 3.11 (bt, 1H), 3.21 (bt, 1H), 3.50-3.55 (m, 1H), 3.72-3.91 (m, 5H), 3.98 (t, J=5.2 Hz, 1H), 4.38 (s, 2H), 4.97-5.00 (m, 2H).

Example 2

Recrystallization of 1.5 Hydrate of Tartrate Salt of Compound 1 (Crystal Form I) from Water 50 g of tartrate salt of Compound 1 obtained from Example 1 was added to 250~500 ml of water, and dissolved in water while adjusting the solution with 10 N NaOH to pH 6~7. 11.7 g of L-tartaric acid dissolved in 23.5 ml of water was added, and crystals were obtained with varying the temperature, stirring rate and stirring time as shown in the following Table 1. Then, the crystals were filtered and dried to obtain the crystal form I. The stirring rate was varied in the range of 50~400 rpm, and the temperature was varied in the range of 5~32° C. The volume of water used for recrystallization, the stirring rate, temperature and stirring time are represented in the following Table 1.

TABLE 1

| Entry | Volume (mL) | RPM | Temperature | Time (h) | Yield (%) |
|---|---|---|---|---|---|
| 1 | 250 | 50 | 25.0 | 0.50 | 96.0 (48.0 g) |
| 2 | 250 | 100 | 25.0 | 1.00 | 92.8 (46.4 g) |
| 3 | 250 | 400 | 25.0 | 5.00 | 93.6 (46.8 g) |
| 4 | 375 | 400 | 25.0 | 1.00 | 92.4 (46.2 g) |
| 5 | 500 | 50 | 25.0 | 5.00 | 46.6 (23.3 g) |
| 6 | 500 | 400 | 25.0 | 3.00 | 88.2 (44.1 g) |
| 7 | 375 | 225 | 31.8 | 2.75 | 94.0 (47.0 g) |
| 8 | 375 | 225 | 15.0 | 2.75 | 91.0 (45.5 g) |
| 9 | 250 | 50 | 5.0 | 0.50 | 81.4 (40.7 g) |
| 10 | 250 | 400 | 5.0 | 5.00 | 101.8 (50.9 g) |

Example 3

Recrystallization of 1.5 Hydrate of Tartrate Salt of Compound 1 (Crystal Form I) from the Mixed Solvent 5 g of tartrate salt of Compound 1 was dissolved in 25~60 ml of solvent mixtures comprised of water and acetonitrile in different ratios. Crystals were precipitated with varying the temperature in the presence or absence of stirring, filtered and dried to recrystallize the tartrate salt of Compound 1. The conditions used for recrystallization are listed in the following Table 2.

TABLE 2

| Entry | Acetonitrile/water | Stirring | Temperature (° C.) |
|---|---|---|---|
| 1 | 4/1 | N | 25.0 |
| 3 | 6/1 | N | 25.0 |
| 4 | 6/1 | N | 0.0 |
| 5 | 8/1 | N | 25.0 |
| 6 | 8/1 | Y | 25.0 |
| 8 | 1/1 | N | 25.0 |
| 9 | 1/1 | Y | 20.0 |

Test Example 1

Powder X-ray Diffractometry

About 20 mg of the sample was charged in the sample holder and mounted on Powder X-ray diffractometer to obtain the diffraction pattern in the range of 3~40°/2θ. The diffraction patterns as obtained are attached to the present specification as FIGS. 1, 5 and 10, respectively. Specific conditions for analysis are as follows.

Instrument: Bruker 4D Endeavor

Time per step: 0.3 s
Stepsize: 0.03°
Scan Mode: step
Voltage/Current: 40 kV/30 mA
Cu-target (Ni-filter)
Divergence slit: 0.3
Detector: PSD: LynxEye Instrument: Philips X-ray Generator (PW1710)

Time per step: 0.5 s
Stepsize: 0.03°
Scan Mode: step
Voltage/Current: 40 kV/30 mA
Cu-target (Ni-filter)
Source Slit: 1.0 mm
Detector Slits: 0.15 mm, 1.0 mm

Test Example 2

Infrared Spectroscopy

Figure 2:
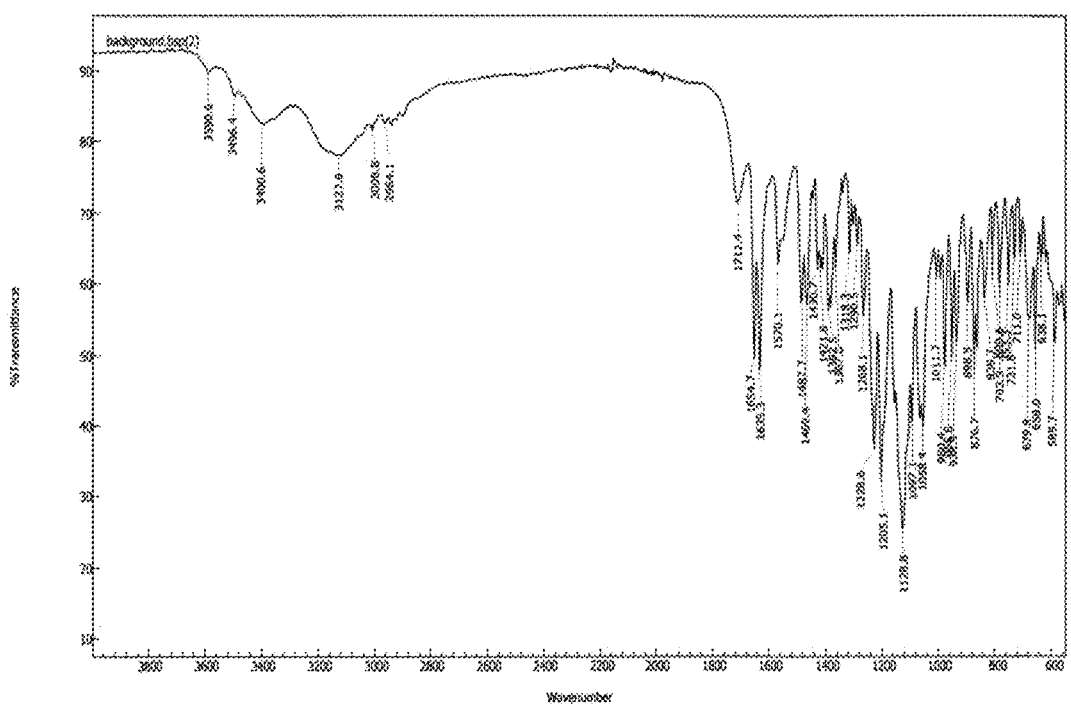
FIG. 2 represents the Infrared spectroscopy (FT-IR) spectrum of the crystal form I as the 1.5 hydrate of tartrate salt of Compound 1.
Figure 6:
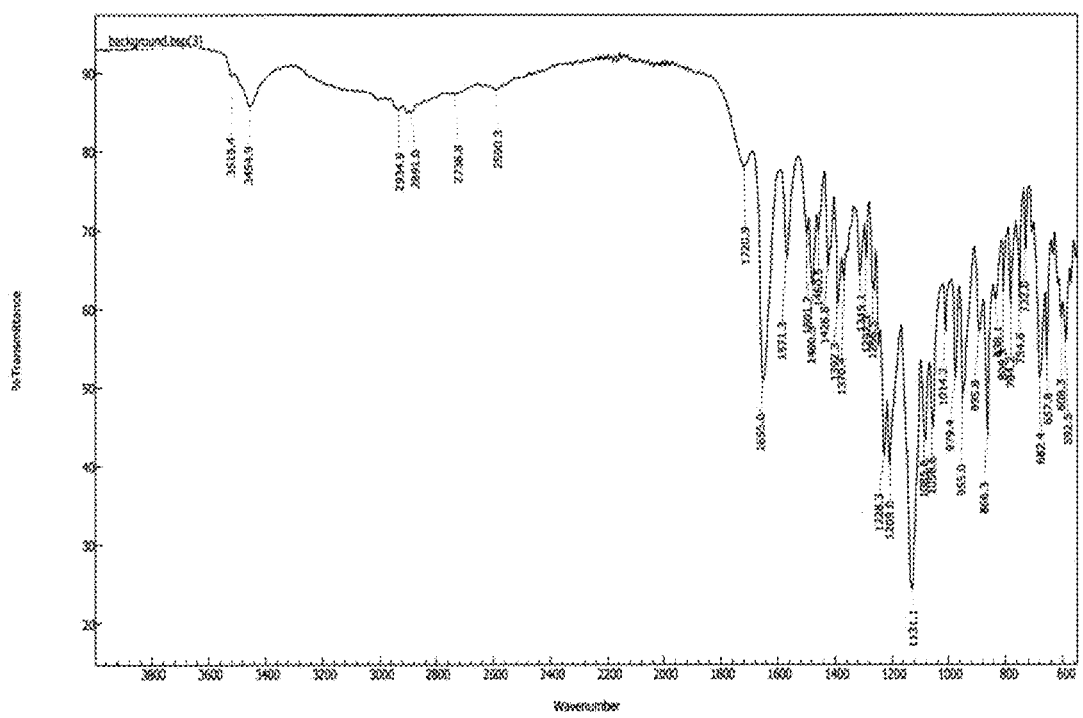
FIG. 6 represents the Infrared spectroscopy (FT-IR) spectrum of the crystal form II as the 0.5 hydrate of tartrate salt of Compound 1.
Figure 11:
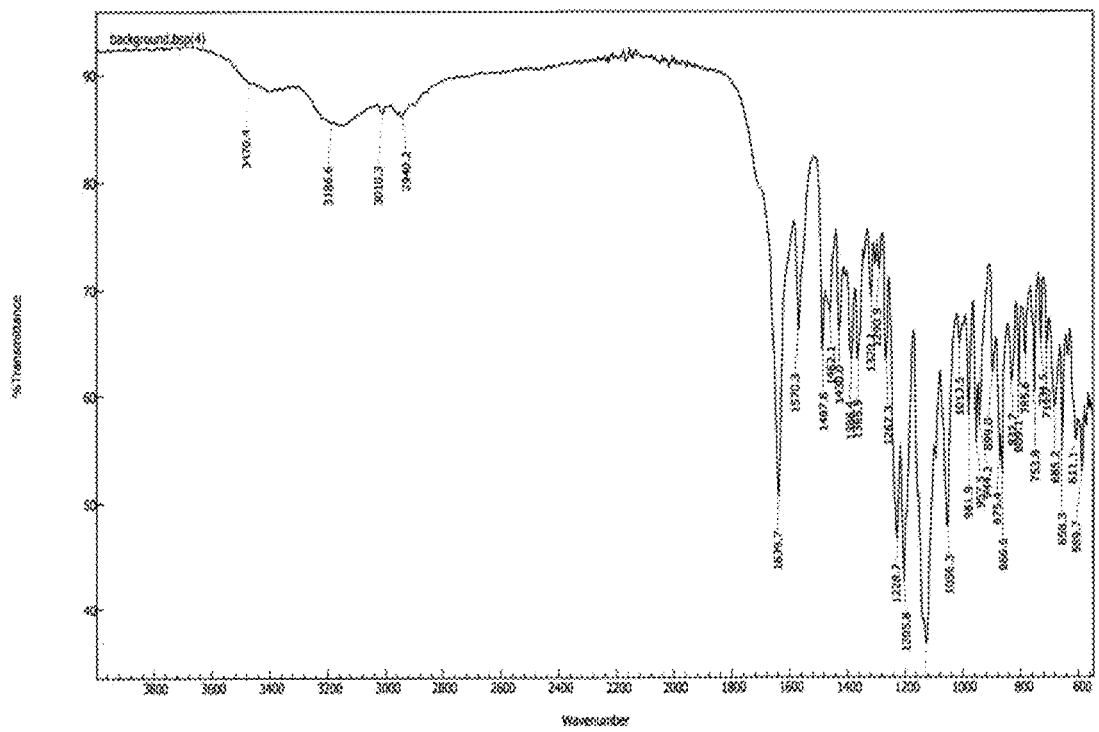
FIG. 11 represents the Infrared spectroscopy (FT-IR) spectrum of the crystal form III as the anhydrate of tartrate salt of Compound 1.

The infrared spectra for respective crystal forms according to the present invention were obtained using ZASCO FT-IR 4200 provided with DTGS detector. The resolution of respective spectra was 4 $cm^{-4}$, and the number of scan was 16. In the present Test Example 1~2 mg of the sample was placed on the accessory of ATR (Attenuated Total Reflectance) and the equipment was operated to obtain the spectrum. Background data was obtained by operating the equipment without any material in ATR. The spectra thus obtained are attached to the present specification as FIGS. 2, 6 and 11, respectively.

Test Example 3

Differential Scanning Calorimetry (DSC)

Differential Scanning calorimetry (DSC) was conducted using Mettler Toledo's DSC821$^e$. About 2~3 mg of the sample was charged into the aluminum pan, and the weight thereof was accurately recorded. The pan was covered with a lid through which a hole was punched. The pan was mounted on the equipment and heated from 25 to 250° C. in the rate of 10° C./min under nitrogen purge. Indium metal was used as the standard for calibration. The spectra thus obtained are attached to the present specification as FIGS. 3, 7 and 12, respectively.

Test Example 4

Thermogravimetry (TG)

Thermogravimetry (TG) was conducted using Mettler Toledo TGA850. About 4~5 mg of the sample was charged into the aluminum pan. The pan was mounted on the equipment and then heated from 25 to 250° C. in the rate of 10° C./min under nitrogen purge. Nickel and Aluminum™ were used as the standard for calibration. The results of TG analysis as obtained are attached to the present specification as FIGS. 3, 7 and 12, respectively, together with the results of DSC analysis according to said Test Example 3.

Test Example 5

Dynamic Vapor Adsorption/Desorption Analysis

The dynamic vapor adsorption/desorption data were collected on VTI-SA Vapor Sorption Analyzer. While maintaining 25° C., the vapor adsorption and desorption were repeated three times at intervals of 5% RH in the range of relative humidity (RH) 5~95%. The samples were not dried prior to the analysis. The equilibrium standard used for analysis was that the weight change within 2 minutes is less than 0.01%.

Figure 4:
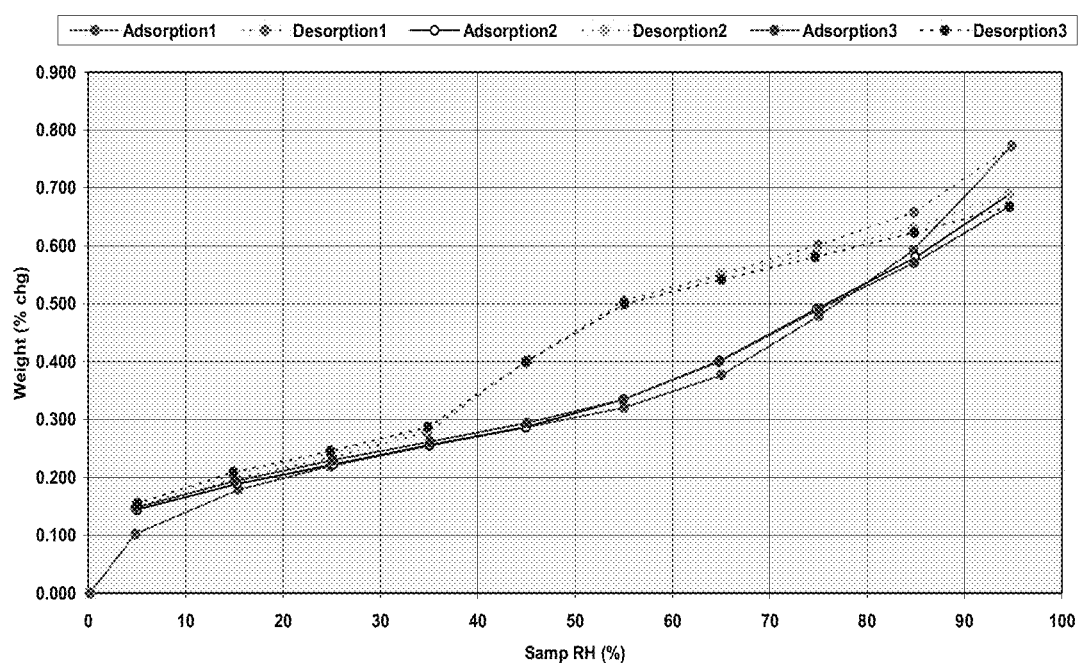
FIG. 4 represents the dynamic vapor adsorption/desorption isotherm of the crystal form I as the 1.5 hydrate of tartrate salt of Compound 1.
Figure 8:
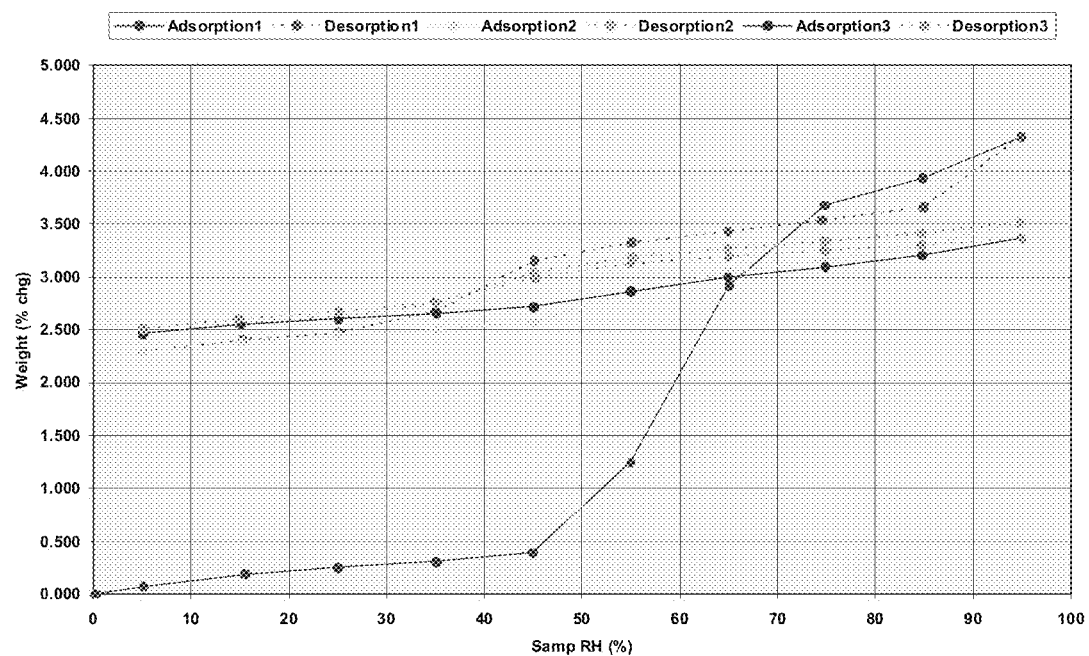
FIG. 8 represents the dynamic vapor adsorption/desorption isotherm of the crystal form II as the 0.5 hydrate of tartrate salt of Compound 1.

As the result of analysis, FIG. 4 shows a result of the vapor adsorption/desorption isotherm of the crystal form I, from which it can be seen that the crystal form I shows the weight change of 0.8% or less according to the change of external humidity in the range of 5~95% RH. That is, the crystal form I according to the present invention is very stable against the change of relative humidity. FIG. 8 shows a result of the vapor adsorption/desorption isotherm of the crystal form II, from which it can be seen that in the crystal form II the weight increases by 4.3% when the relative humidity is raised up to 95% in the initial moisture adsorption test. After moisture desorption, the crystal form II gives the same graph of moisture behavior as the crystal form I. From such result, it could be confirmed that the crystal form II was converted into the crystal form I during the course of the initial moisture adsorption. FIG. 13 shows a result of the vapor adsorption/desorption isotherm of the crystal form III, from which it can be seen that in the crystal form III the weight increases by 3.6% when the relative humidity is raised up to 95%. Furthermore, it can be seen that decreasing the humidity causes the moisture desorption of 0.6% or less so that the crystal form III becomes to contain the same moisture content as the crystal form I.

Test Example 6

Powder X-ray Diffraction Test of the Crystal Form II During Moisture Adsorption

Figure 9:
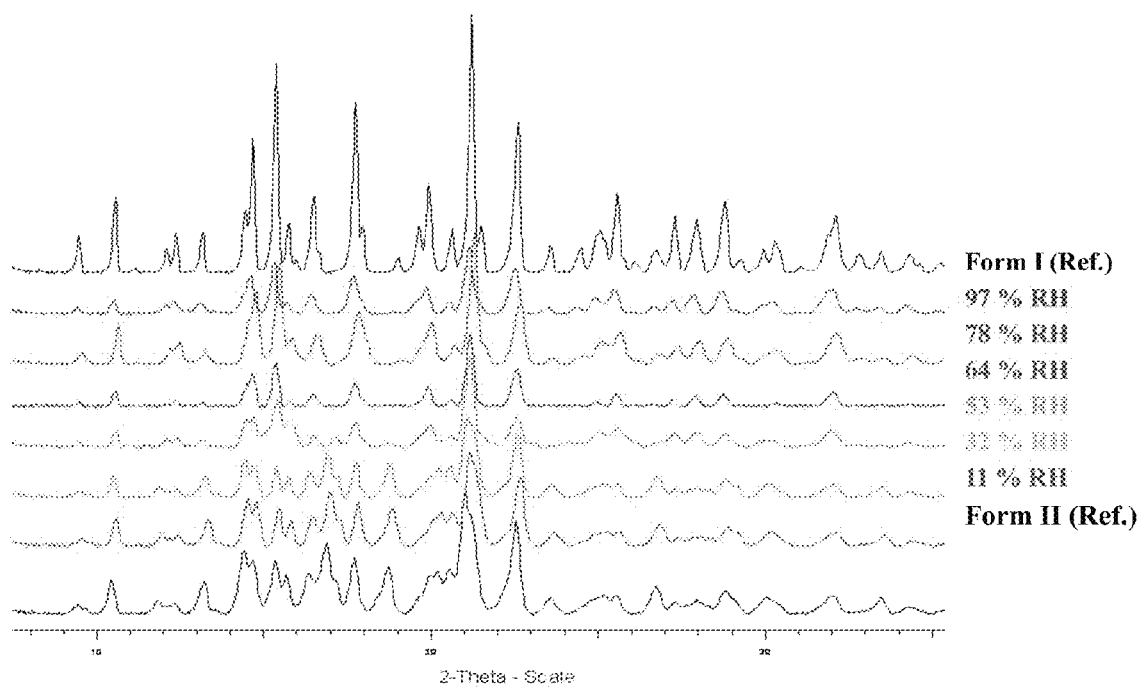
FIG. 9 represents the X-ray powder diffraction (XRD) spectrum of the crystal form II as the 0.5 hydrate of tartrate salt of Compound 1, during the course of moisture adsorption study.

About 50 mg of the crystal form II was placed in a glass vial, put under the relative humidity of 11%, 32%, 53%, 64%, 78% and 97%, respectively, for two or more days to induce the moisture adsorption, and then subjected to the powder X-ray diffraction test according to the conditions as presented in said Test Example 1 to identify any change of the crystal form at the time of moisture adsorption (see FIG. 9).

Respective relative humidity was provided by making the saturated aqueous solution of salt as shown in the following Table 3 and placing the solution in a desiccator, which was then sealed.

TABLE 3

| | |
|---|---|
| Relative humidity 11% | Saturated aqueous solution of LiCl |
| Relative humidity 32% | Saturated aqueous solution of $MgCl_2$ |
| Relative humidity 53% | Saturated aqueous solution of $Mg(NO_3)_2 \cdot 6H_2O$ |
| Relative humidity 64% | Saturated aqueous solution of $NaNO_2$ |
| Relative humidity 78% | Saturated aqueous solution of NaCl |
| Relative humidity 97% | Saturated aqueous solution of $KNO_3$ |

Test Example 7

Powder X-ray Diffraction Test of the Crystal Form III During Moisture Adsorption The crystal form III was placed on a XRD holder and subjected to XRD test over the time (after 30 minutes, 1 hour and 5 hours) while allowing the moisture adsorption at room temperature under atmosphere (see FIG. 15). In addition, the weight change at room temperature under atmosphere was recorded by times to obtain a graph (see FIG. 14). It could be known that the crystal form III rapidly absorbs water so that it is converted into the crystal form I within about one hour.

Test Example 8

Thermal Stability of the Crystal Form I and the Crystal Form II

About 50 mg of each of the crystal form I and the crystal form II was placed in Duma bottle, and then kept at 40±2° C., 75±5% RH or 60±2° C., 5±5% RH. After 2 weeks, 4 weeks and 8 weeks, each sample was removed from Duma bottle and analyzed by XRD for identifying any change of the crystal form and HPLC for identifying the stability. For HPLC analysis the sample was dissolved in a mixture of acetonitrile/water/trifluoroacetic acid=30/70/0.1 (v/v/v) and then subjected to the analysis. The conditions for HPLC analysis are as follows:

Conditions for HPLC Analysis

Column: Atlantis dC18 (4.6 mm I.D×250 mm L, Particle Size 5, μm, Waters)
Column Temperature: 10° C.
Mobile phase:
Mobile phase A: MeCN/TFA=100/0.1 (v/v)
Mobile phase B: H$_2$O/TFA=100/0.1 (v/v)
Gradient condition:

| Time (min.) | A (%) | B (%) |
|---|---|---|
| Initial | 38 | 62 |
| 25 | 38 | 62 |
| 35 | 80 | 20 |
| 40 | 38 | 62 |
| 55 | 38 | 62 |

Flow rate: 0.7 ml/min.
Detection: 256 nm, UV
Injection volume: 10 μl
Total analysis time: 55 min.

The results of the stability for the crystal form I and the crystal form II are shown in the following Table 4.

TABLE 4

| | 40° C./75% RH | | 60° C./5% RH | |
|---|---|---|---|---|
| Time (week) | Crystal form I | Crystal form II | Crystal form I | Crystal form II |
| 0 | 99.4 | 98.4 | 99.4 | 98.4 |
| 2 | 99.3 | 98.4 | 98.8 | 98.1 |
| 4 | 99.2 | 98.3 | 98.6 | 97.8 |
| 8 | 99.2 | 98.2 | 98.4 | 97.5 |

Figure 16:
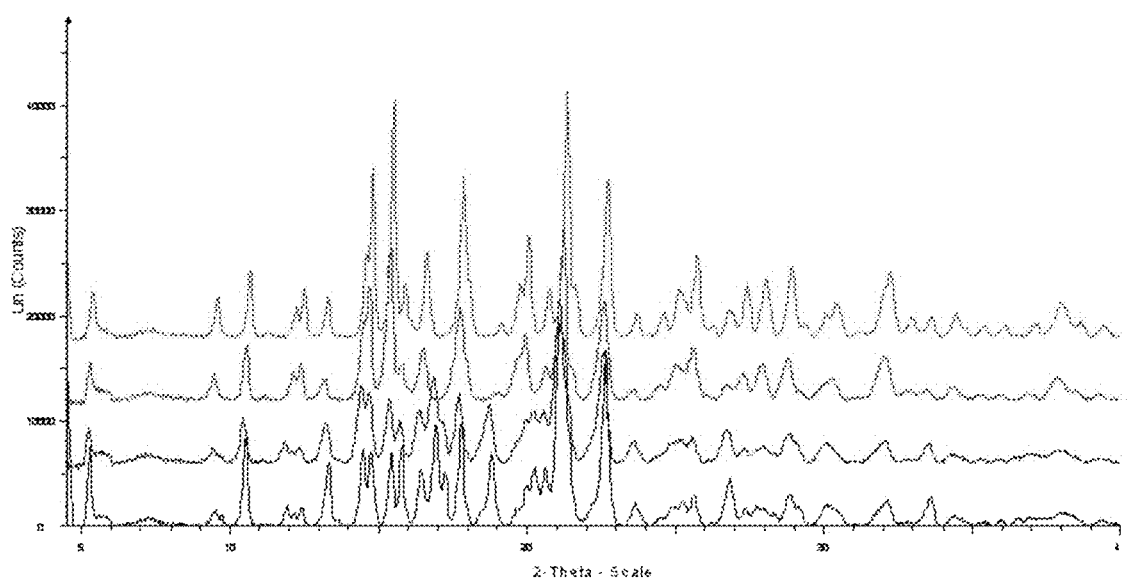
FIG. 16 represents the X-ray powder diffraction (XRD) spectrum obtained after conducting the experiment of Test Example 8, indicating XRD of the crystal form II, XRD of the sample of the crystal form II after 8-week storage at 60° C./5% RH, XRD of the sample of the crystal form II after 8-week storage at 40° C./75% RH, and XRD of the crystal form I, in the order from the bottom.

As shown in Table 4, it could be confirmed that upon keeping the crystal form I and the crystal form II at 40±2° C., 75±5% RH or 60±2° C., 5±5% RH they exhibit a superior stability up to 8 weeks. However, according to the result of XRD analysis the crystal form I did not show any change up to 8 weeks, but the crystal form II was converted into the crystal form I at 8 week under the condition of 40° C./75% RH (see FIG. 16).

Test Example 9

Determination of Density of the Crystal Form I and the Crystal Form II

About 20~30 ml of each of the crystal form I and the crystal form II was introduced into a 50 ml measuring cylinder. Here, the samples were slowly introduced so that they are not closely contacted with each other. After reading a scale on the measuring cylinder, the weight thereof was measured to calculate the bulk-density. After measuring the bulk-density, the measuring cylinder containing the sample was put on ERWEKA densitometer and then subjected to impulses 250 times to measure the tapdensity (Table 5). The result of measurement shows that both the bulk-density and the tap-density of the crystal form I were higher than those of the crystal form II. The Can index was calculated from the bulk-density and the tap-density. As a result, it was lower in the crystal form I than in the crystal form II. Since it is generally understood that the lower the Carr index, the better the flowability, it could be identified by comparing the Carr indexes that the crystal form I can be easily handled in processing procedures including tabletting as compared to the crystal form II.

TABLE 5

Determination of density and particle size of the crystal form I and the crystal form II

| | Density | | |
|---|---|---|---|
| Form | Bulk-density | Tap-density | Carr index |
| I | 0.45 | 0.54 | 16.22 |
| II | 0.34 | 0.44 | 23.47 |

The invention claimed is:

1. 1.5 Hydrate of 1-{(2S)-2-amino-4-[2,4-bis(trifluoromethyl)-5,8-dihydropyrido[3,4-d]pyrimidin-7(6H)-yl]-4-oxobutyl}-5,5-difluoropiperidin-2-one tartrate salt having a water content in the range of 3.5-5.5%.

2. The 1.5 hydrate according to claim 1, wherein characteristic peak values (2θ) in XRD diffractogram are 15, 18, 20, 21 and 23°.

3. A process for preparing the 1.5 hydrate according to claim 1, characterized in that 1-{(2S)-2-amino-4-[2,4-bis(trifluoromethyl)-5,8-dihydropyrido[3,4-d]-pyrimidin-7(6H)-yl]-4-oxobutyl}-5,5-difluoropiperidin-2-one tartrate salt is recrystallized from water, acetonitrile/water, ethanol/water, ethanol/hexane or ethyl acetate/hexane solvent.

4. The process according to claim 3, wherein the recrystallizing solvent is water.

5. A pharmaceutical composition for inhibiting DPP-IV, which comprises the 1.5 hydrate according to claim 1 as the active component together with a pharmaceutically acceptable carrier.

6. The composition according to claim 5, wherein it is used for the treatment of diabetes or obesity.

* * * * *